(12) United States Patent
Tung et al.

(10) Patent No.: US 7,700,815 B2
(45) Date of Patent: Apr. 20, 2010

(54) METHOD FOR PRODUCING FLUORINATED ORGANIC COMPOUNDS

(75) Inventors: Hsueh Sung Tung, Getzville, NY (US);
Rajiv R. Singh, Getzville, NY (US);
Michael Van Der Puy, Amherst, NY (US)

(73) Assignee: Honeywell International Inc, Morristown, NJ (US)

( * ) Notice: Subject to any disclaimer, the term of this patent is extended or adjusted under 35 U.S.C. 154(b) by 152 days.

(21) Appl. No.: 11/863,645

(22) Filed: Sep. 28, 2007

(65) Prior Publication Data

US 2009/0088593 A1 Apr. 2, 2009

(51) Int. Cl.
*C07C 17/00* (2006.01)
(52) U.S. Cl. .................. 570/153; 570/156; 570/157
(58) Field of Classification Search .................. 570/153
See application file for complete search history.

(56) References Cited

U.S. PATENT DOCUMENTS 5,157,171 A 10/1992 Sievert et al.
5,396,000 A 3/1995 Nappa et al.
5,679,875 A 10/1997 Aoyama et al.
6,031,141 A 2/2000 Mallikarjuna et al.
6,548,719 B1 4/2003 Nair et al.
2006/0106263 A1 5/2006 Miller et al.

FOREIGN PATENT DOCUMENTS

WO 98/33755 8/1998

OTHER PUBLICATIONS

Belen'kii, G. G. et al., "Electrophilic, catalytic alkylation of polyfluoroolefins by some fluoroalkanes," Journal of Fluorine Chemistry, 108, pp. 15-20 (2001).

*Primary Examiner*—Sikarl A Witherspoon
(74) *Attorney, Agent, or Firm*—Bruce Bradford

(57) ABSTRACT

Disclosed is a method for producing fluorinated organic compounds, including petnafluoropropenes, which preferably comprises converting at least one compound of formula (I):

$$CF_nX_mCF_aX_bCH_2X \qquad (I)$$

to at least one compound of formula (II)

$$CF_3CF=CHF \qquad (II)$$

where each X is independently Cl, I or Br; n is 2 or 3; m is 0 or 1, a is 1 or 2, b is 0 or 1, m+n=3 and a+b=2.

10 Claims, No Drawings

METHOD FOR PRODUCING FLUORINATED ORGANIC COMPOUNDS

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) and pentafluoropropenes (1,2,3,3,3-pentafluoropropene (HFO-1225ye) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 5,679,875 discloses methods for manufacturing 1,1,1,2,3-pentafluoropropene and 1,1,1,2,3-pentafluoropropane; U.S. Pat. No. 6,031,141 discloses a catalytic process using chromium-containing catalysts for the dehydrofluorination of hydrofluorocarbons to fluoroolefins; U.S. Pat. No. 5,396,000 discloses a process for producing CF3CHFCH2F utilizing a vapor phase catalytic dehydrofluorination step to produce CF3CF=CHF from CF3CHFCHF2; U.S. Pat. No. 6,548,719 discloses a process for producing fluoroolefins by dehydrohalogenating a hydrofluorocarbon in the presence of a phase transfer catalyst; U.S. Publication No. 2006/0106263 discloses the production and purification of hydrofluoroolefin compounds; and WO98/33755 discloses catalytic process for the dehydrofluorination of hexafluoropropanes to pentafluoropropenes.

Notwithstanding prior teachings applicants appreciate a continuing need for methods of efficiently preparing certain hydrofluorocarbons, particularly pentafluorpropenes such as HFO-1225, including particularly HFO-1225ye.

SUMMARY OF THE INVENTION

In one aspect of the present invention, applicants have developed methods for producing fluorinated organic compounds, including hydrofluoroolefins in general and pentafluoropropenes in particular embodiments, which preferably comprises converting at least one compound of formula (I):

to at least one compound of formula (II):

where each X is independently Cl, I or Br; n is 2 or 3; m is 0 or 1; a is 1 or 2; b is 0 or 1; m+n=3; and a+b=2.

The preferred converting step of the present invention comprises catalytic reaction of the compound of formula (I). The catalytic reaction step comprises in preferred embodiments introducing said compound of formula (I) to a reaction system under conditions effective to convert, and preferably convert at least about 50%, more preferably at least about 65%, even more preferably at least about 90%, and even more preferably at least about 95% of said compound of formula (I). It is also generally preferred that said converting step produces a reaction product having at least about 60% selectivity, more preferably at least about 70% selectivity and even more preferably at least about 90% selectivity, to compounds of formula (II), preferably HFO-1225ye. In certain highly preferred embodiment the selectivity to pentatetrafluoropropene is at least about 95%.

DETAILED DESCRIPTION OF PREFERRED EMBODIMENTS

One beneficial aspect of the present invention is that it enables the production of desirable fluoroolefins, such as HFO-1225ye, using relatively high conversion and high selectivity reactions. In addition, the methods of the present invention provided reactions with relatively high yield and relatively high selectivity.

In one preferred aspect of the present invention the reactant comprises a compound of formula I in which n is 3, m is 0, a is 2 and b is 0, namely, $CF_3CF_2CH_2Cl$, which is preferably converted in substantially single reaction step to the compound of formula (II). The starting compound in such embodiments, namely $CF_3CF_2CH_2Cl$, can be prepared by methods known in the art, including those outlined above, the conversion of $CF_3CF_2CH_2OH$ via the tosylate, and/or the reduction of $CF_3CF_2CHCl_2$.

In another preferred aspect of the present invention the reactant comprises a compound of formula I in which n is 3, m is 0, a is 1 and b is 1, namely, $CF_3CFXCH_2Cl$. For convenience, such compounds are sometimes referred to herein for convenience as compounds of formula (IA). In preferred aspects of such formula (IA) embodiments, X is Cl.

In another preferred aspect of the present invention the reactant comprises a compound of formula I in which n is 2, m is 1, a is 2 and b is 0, namely, $CF_2XCF_2CH_2Cl$. For convenience, such compounds are sometimes referred to herein for convenience as compounds of formula (IB). In preferred aspects of such formula (IB) embodiments, X is Cl.

Conversion of Formula (I) Compounds

The methods of the present invention preferably comprise converting a compound of formula (I) to a fluorolefin, preferably a C3 fluorolefin, more preferably a compound of formula (II), and even more preferably pentafluoropropene.

In certain preferred embodiments, the present converting step is carried out under conditions effective to provide a formula (I) conversion of at least about 40%, more preferably at least about 55%, and even more preferably at least about 70%. In certain preferred embodiments the conversion is at least about 90%, and more preferably about 100%. Further in certain preferred embodiments, the conversion of the compound of formula I to produce a compound of formula II is conducted under conditions effective to provide a formula II selectivity of at least about 25%, more preferably at least about 40%, more preferably at least about 70%, and even more preferably at least about 90%.

This reaction step can be carried out in the liquid phase or in the gas phase, or in a combination of gas and liquid phases, and it is contemplated that the reaction can be carried out batch wise, continuous, or a combination of these. Preferably, however, the reaction is carried out as a gas phase reaction.

For example, in embodiments in which the starting compound comprises 1,1,1,2,2-pentafluoro-3-chloropropane ($CF_3CF_2CH_2Cl$), a catalyzed gas phase reaction is generally preferred. Although it is contemplated that in such embodiments the reaction step may be preformed using a wide variety of process parameters and process conditions in view of the overall teachings contained herein, it is preferred in such embodiments the catalyst is preferably a carbon- and/or metal-based catalyst, such as activated carbon, fluorinated chromium oxide or fluorinated alumina, with or without added metal salts such as those of cobalt, nickel, barium, magnesium, zinc, or cesium. It is expected that many other catalysts may be used depending on the requirements of particular embodiments in view of the teachings contained herein. Of course, two or more any of these catalysts, or other catalysts not named here, may be used in combination.

In general it is preferred that the catalysts are fluorinated, preferably for a period of from about several hours (eg., 6 hours). In preferred embodiments, fluorination of the catalysts comprises exposing the catalyst to a stream of HF at about reaction temperature and under slight pressure, for example about 5-150 psia.

The gas phase reaction may be conducted, for example, by introducing a gaseous form of a compound of formula (I), and preferably $CF_3CF_2CH_2Cl$, a compound of formula (IA), a compound of formula (IB), and combinations of these, and optionally HF, into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with suitable means to heat the reaction mixture to the desired reaction temperature.

The use of HF is not believed to be necessary as a reactant to effectively conduct the present methods, but is nevertheless preferred in certain embodiments. For example, for processes in which the starting materials include compounds of Formula (IA), Formula (IB) or combinations of these, it is generally preferred that at least one mole of HF per mole of dichlorotetrafluoropropane is used. The mole ratio of HF:dichlorotetrafluoropropane used in such embodiments preferably is in the range of from about 1:1 to about 9.5:1, and even more preferably from about 1:1 to about 8:2.

While it is contemplated that a wide variety of reaction temperatures may be used, depending on relevant factors such as the catalyst being used and the most desired reaction product, it is generally preferred that the reaction temperature is from about 200° C. to about 600° C., preferably about 375° C. to about 550° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum, and in certain preferred embodiments is from about 15 to about 120 psia.

It is contemplated that the amount of catalyst use will vary depending on the particular parameters present in each.

Although applicant does not intend to be bound to or limited by any particular theory of operation, it is believed that the following reaction scheme represents the preferred operation of the present invention in which the compound of Formula I is $CF_3CF_2CH_2Cl$:

$CF_3CF_2CH_2Cl \rightarrow CF_3CF\!=\!CHCl + HF$ $CF_3CF\!=\!CHCl + HF \rightarrow CF_3CHFCHFCl$ $CF_3CHFCHFCl \rightarrow CF_3CF\!=\!CHF + HCl$ Generally, the reaction is represented as follows:

$CF_3CF_2CH_2Cl \rightarrow CF_3CF\!=\!CHF + HCl$

For reactions in which the reactant comprises compounds of formula (IA) or (IB), including particularly $ClCF_2CF_2CH_2Cl$ and $CF_3CFClCH_2Cl$, respectively, the following reaction sequences are deemed likely:

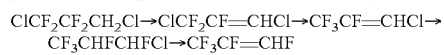

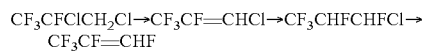

Formation of Compounds of Formula (I)

The present invention also involves in one aspect methods for forming compounds of formula (I), and most preferably $CF_3CF_2CH_2Cl$ comprising reacting tetrafluoroethylene with $CH_2FCl$. The use of such methods may be advantageous because ethylene and its halogentated derivates, such as tertrafluorethylene, are relatively easy to handle, and are generally readily available in commercial quantities and/or can be easily produced from other readily available materials. In certain embodiments, therefore, the compounds of formula (I) are preferably synthesized by the catalyzed gas phase addition of $CH_2FCl$ and $CF_2\!=\!CF_2$.

In certain preferred embodiments, the addition step comprises contacting, (preferably by introducing into a reactor) the $CH_2FCl$ with $CF_2\!=\!CF_2$ in a $CH_2FCl:CF_2\!=\!CF_2$ mole ratio of from about 1:1 to about 200:1, and even more preferably of from about 1.5:1 to about 2:1

It is contemplated that this reaction step can be carried out in the liquid phase or in the gas phase, or a combination of liquid/gas phases, and it is further contemplated that the reaction can be carried out batch wise, continuous, or a combination of these. However, it is preferred that this reaction step comprise a gas phase reaction, preferably in the presence of catalyst, supported on carbon or unsupported, preferably a metal-based catalyst, such as antimony-based catalysts (such as $SbF_3$, $SbF_5$, and partially fluorinated $SbCl_3$ or $SbCl_5$) aluminum-based catalyst (such as $AlCl_3$), iron-based catalyst such $FeCl3$ including such catalysts on a carbon or other appropriate support. It is expected that many other catalysts may be used depending on the requirements of particular embodiments, and of course, two or more any of these catalysts, or other catalysts not named here, may be used in combination.

While it is contemplated that a wide variety of reaction temperatures and pressures may be used, depending on relevant factors such as the catalyst being used and the most desired reaction product, it is generally preferred that at least a portion of the addition step is carried out at a reaction temperature of from about 5 to about 1000° C., and even more preferably from about 40 to about 60° C. for reactors which are preferably maintained at a pressure of from about 1 to about 1500 psig, and even more preferably from about 20 to about 40 psig.

In certain preferred embodiments, the reactants are introduced into an appropriate reaction vessel in the form of a gas and the reactor is preferably maintained at a temperature of about 50° C. and the reactor is preferably maintained at a pressure of about 30 psig.

EXAMPLES

Additional features of the present invention are provided in the following examples, which should not be construed as limiting the claims in any way.

Example 1

This example illustrates the reaction of TFE with $CH_2FCl$ in a gas phase reaction. Into a ½ inch flow reactor (Monel) 50 grams of freshly prepared catalyst (as indicated below) are charged. $CF_2=CF_2$ (TFE) and $CH_2FCl$ (R31) are passed through a mass flow controller with a desired flow rate (as indicated below) to the preheater from respective cylinders connected with regulators. The preheater was connected to the reactor and always kept 10° C. below the reactor temperature. The reactor was uniformly heated to the desired temperature by an external heating element with an automatic control. The exit line from the reactor was connected to an on-line GC and GCMS for analysis. A 15 wt % KOH scrubber solution was used at 50° C. to neutralize acids coming out from the reactor. The gas stream coming out of the scrubber solution was then condensed in a cylinder under liquid $N_2$ and then finally fractionated (distilled) to isolate products. $SbF_5/C$ and $AlCl_3/C$ are used as the catalyst. At 50° C. and under 30 psig reactor pressure, 50 sccm of TFE and 150 sccm of $CH_2FCl$ were passed over $SbF_5/C$ to achieve a 26% conversion of TFE and an 82% selectivity to $CF_3CF_2CH_2Cl$. When $AlCl_3/C$ is used as the catalyst, a 35% conversion and 78% selectivity to $CF_3CF_2CH_2Cl$ is obtained.

Example 2

This example illustrates the preparation of $CF_3CF_2CH_2Cl$ by reacting TFE with $CH_2FCl$ in a batch reactor. Thus, into a 300 ml autoclave, 0.1 mol $C_2F_4$ was reacted with 0.2 mol $CH_2ClF$ in the presence of 0.05 mol of $AlCl_3$ at 20-30° for 3 hr to give 60% yield to $CF_3CF_2CH_2Cl$ which was then isolated and purified by distillation.

Example 3

This example illustrates the reaction of CTFE with $CH_2FCl$ in a gas phase reaction. Example 1 is repeated expect that CTFE is used in place of TFE. The major reaction products include $CF_3CFClCH_2Cl$ and $CF2ClCF2CH2Cl$ at a CTFE conversion of 21%.

Example 4

This example illustrates the reaction of CTFE with $CH_2FCl$ in batch reactor. Into a 300 ml autoclave, 0.1 mol $C_2F_4$ was reacted with 0.2 mol $CH_2FCl$ in the presence of 0.05 mol of $AlCl_3$ at 20-30° for 3 hr to give a 60% yield of $CF_3CF_2CH_2Cl$ which was isolated and purified by distillation.

Example 5

This example illustrates the gas phase conversion of $CF_3CF_2CH_2C_1$ to $CF_3CF=CHF$. A 22-inch (½-inch diameter) Monel tube reactor is charged with 120 cc of chromium oxyfluoride catalyst. The reactor is mounted inside a heater with three zones (top, middle and bottom). The inlet of the reactor is connected to a pre-heater, which was kept at 300° C. by electrical heating. Organic is fed from a cylinder kept at 65° C. HF was introduced similarly to the pre-heater. An on-line GC and a GCMS are used to analyze samples taken at the reactor exit line at regular time intervals. The reactor effluent is introduced into a 20-60% KOH scrubber solution, and the effluent from the scrubber solution is then condensed to collect the products. The desired product, $CF_3CF=CHF$, is isolated from the mixture by distillation. The conversion of $CF_3CF_2CH_2Cl$ is from about 50% to about 100% and the selectivity to $CF_3CF=CHF$ is from about 60% to about 100%, depending on the reaction conditions. The major byproducts were $CF_3CF=CHCl$ and CF3CHFCHClF.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising converting in a gas phase at least one compound of formula (I):

to at least one compound of formula (II):

where each X is independently Cl, I or Br; n is 2 or 3; m is 0 or 1; a is 1 or 2; b is 0 or 1; m+n=3; and a+b=2.

2. The method of claim 1 wherein said compound of formula (I) is formed by a method comprising reacting a fluorinated C2 olefin with $CH_2FCl$.

3. The method of claim 2 wherein said fluorinated C2 olefin comprises tetrafluoroethylene.

4. The method of claim 1 wherein said converting step is carried out under conditions effective to provide a formula (I) conversion of at least about 40%.

5. The method of claim 1 wherein said converting step is carried out under conditions effective to provide a formula (I) conversion of at least about 90%.

6. The method of claim 4 wherein said converting step is carried out under conditions effective to provide a formula (II) selectivity of at least about 40%.

7. The method of claim 5 wherein said converting step is carried out under conditions effective to provide a formula (II) selectivity of at least about 90%.

8. The method of claim 1 wherein said converting step comprises introducing said compound of formula (I) into a reactor containing catalyst or combination of catalysts.

9. The method of claim 8 wherein said catalyst is selected from the group consisting of carbon, activated carbon, fluorinated chromium oxide, fluorinated alumina and combinations of these.

10. The method of claim 1 wherein said converting step is a continuous process.

* * * * *